(12) United States Patent
Kaufmann et al.

(10) Patent No.: US 9,047,398 B2
(45) Date of Patent: Jun. 2, 2015

(54) AMBULATORY MEDICAL DEVICE WITH ALERT CONTROLLER

(75) Inventors: Heiner Kaufmann, Bern (CH); Joerg Dogwiler, Bergdietikin (CH); Edgar Jeanbourquin, Rufenacht (CH); Bastian Perroset, Moosseedorf (CH)

(73) Assignee: Roche Diagnostics International AG, Rotkreuz (CH)

( * ) Notice: Subject to any disclaimer, the term of this patent is extended or adjusted under 35 U.S.C. 154(b) by 1148 days.

(21) Appl. No.: 13/025,691

(22) Filed: Feb. 11, 2011

(65) Prior Publication Data

US 2011/0205066 A1 Aug. 25, 2011

Related U.S. Application Data

(63) Continuation of application No. PCT/EP2009/005449, filed on Jul. 28, 2009.

(51) Int. Cl.
 G08B 23/00 (2006.01)
 A61B 5/00 (2006.01)
 G06F 19/00 (2011.01)

(52) U.S. Cl.
 CPC ........ *G06F 19/3456* (2013.01); *G06F 19/3406* (2013.01)

(58) Field of Classification Search
 CPC .................. G06F 19/3406; G06F 19/3456
 USPC ........ 340/573.1, 545, 506; 604/131; 600/347, 600/365
 See application file for complete search history.

(56) References Cited

U.S. PATENT DOCUMENTS

| | | | |
|---|---|---|---|
| 6,878,132 B2 | 4/2005 | Kipfer | |
| 7,282,029 B1 * | 10/2007 | Poulsen et al. | 600/300 |
| 7,399,277 B2 * | 7/2008 | Saidara et al. | 600/300 |
| 7,570,989 B2 * | 8/2009 | Baura et al. | 600/513 |
| 8,487,758 B2 * | 7/2013 | Istoc | 340/539.15 |
| 8,514,086 B2 * | 8/2013 | Harper et al. | 340/573.1 |
| 8,579,853 B2 * | 11/2013 | Reggiardo et al. | 604/65 |
| 2004/0172222 A1 * | 9/2004 | Simpson et al. | 702/189 |
| 2005/0038332 A1 * | 2/2005 | Saidara et al. | 600/347 |
| 2008/0033357 A1 * | 2/2008 | Mann et al. | 604/131 |
| 2008/0246629 A1 * | 10/2008 | Tsui et al. | 340/870.07 |
| 2008/0294462 A1 * | 11/2008 | Nuhaan et al. | 705/3 |
| 2008/0300572 A1 * | 12/2008 | Rankers et al. | 604/504 |

OTHER PUBLICATIONS

International Search Report, Appln. No. PCT/EP2009/005449, 4 pages, Apr. 6, 2010.
Written Opinion of the International Search Report, Appln. No. PCT/EP2009/005449, 5 pages.

* cited by examiner

*Primary Examiner* — Steven Lim
*Assistant Examiner* — Hongmin Fan
(74) *Attorney, Agent, or Firm* — Dinsmore & Shohl LLP

(57) ABSTRACT

An ambulatory medical device is disclosed. The device comprises a device controller, an alert controller, and an indicator. The device controller may be configured to control the operation of the ambulatory medical device. The alert controller may be configured to: determine a first alerting interval, the first alerting interval defining an earliest point in time and a latest point in time for an alert generation due to a first alerting cause; determine in the first alerting interval an alerting point in time based on an alerting criterion; and generate an alert trigger at the alerting point in time. The indicator may be configured to generate an alert upon generation of the alert trigger. The alerting criterion may be used to generate an alert within the alerting interval at a time especially suited and/or convenient for the device user.

21 Claims, 7 Drawing Sheets

AMBULATORY MEDICAL DEVICE WITH ALERT CONTROLLER

CROSS REFERENCE TO RELATED APPLICATIONS

This application is a continuation of International Application No. PCT/EP2009/005449 filed Jul. 28, 2009 which claims priority to European Patent Application No. 08014273.0 filed on Aug. 11, 2008, which are incorporated by reference herein.

TECHNICAL FIELD

The following disclosure relates generally to an ambulatory medical device, and in particular to a ambulatory medical device with an alert controller.

BACKGROUND

Typical extracorporeal insulin pumps are carried by a patient night and day and are manufactured, among others, by Disetronic Medical Systems AG, Switzerland. Below, reference is mainly made to extracorporeal insulin pumps for illustrative purposes without excluding other ambulatory devices.

Insulin pumps may require a number of service operations to be performed by the user, for example, service operations for replacing disposables. While some of those disposables have a specified lifetime, the lifetime of other disposables is highly dependent on the individual application conditions and may vary in a large range. For example, a typical drug cartridge stores a maximum of 3 ml or 300 IU (International units) of insulin and may have an average lifetime of one week or even more than one week for a first patient. In another example, a typical drug cartridge storing a maximum of 3 ml or 300 IU (International units) of insulin may have an average lifetime of 3 days for a second patient. Furthermore, the lifetime of many disposables is not constant but shows a significant variability even for one and the same patient or user. Alerts are provided by insulin pumps to inform the user about upcoming service operations and may comprise an acoustic and/or tactile indication. Such alerts, however, are often felt as bothersome and inconvenient.

In order to reduce inconvenience resulting from the need for replacing disposable and carrying out further service operations, insulin pumps are available, such as the Omni-Pod® system from Insulet Corporation, USA, which reduce the operation to replacing the infusion pump as a whole every few days. However, those disposable pumps are critical with respect to long-term costs, as well as waste generation and wearing comfort for some users.

While a variety of convenient, cost-effective ambulatory medical devices may exist, it is believed that no one prior to the inventors has made or used the inventive examples as described herein.

SUMMARY

In some examples, disclosed are ambulatory medical devices that may provide improved user acceptance and convenience. The ambulatory medical device may comprise: a device controller, the device controller being configured to control the operation of the ambulatory medical device; an alert controller, the alert controller being configured to determine a first alerting interval, the first alerting interval defining an earliest point in time and a latest point in time for an alert generation due to a first alerting cause, determine in the first alerting interval an alerting point in time based on an alerting criterion, and generate an alert trigger at the alerting point in time; and an indicator, the indicator being configured to generate an alert upon generation of the alert trigger.

While the specification concludes with claims, which particularly point out and distinctly claim the invention, it is believed the present invention will be better understood from the following description of certain examples taken in conjunction with the accompanying drawings. In the drawings, like numerals represent like elements throughout the several views.

DETAILED DESCRIPTION

Figure 1:
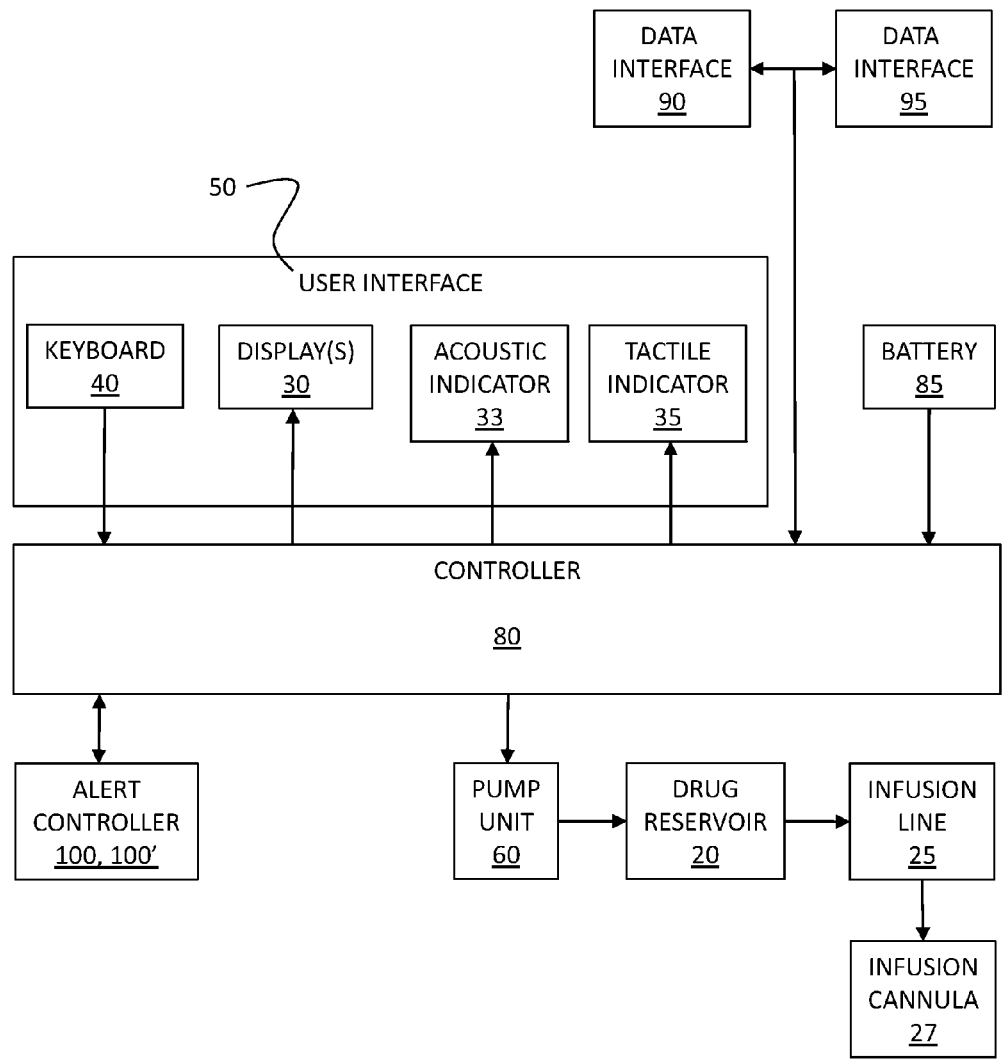
FIG. 1 depicts the internal structure of an exemplary version of a ambulatory medical device.

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

The term 'Disposable' refers to elements which are required for operating the portable medical device according to its intended use and only have a limited lifetime after which they have to be replaced, exchanged or refurbished. The term 'Replacing' is used in the following for all of those actions. In most cases, the disposables are discarded after use.

The terms 'Exploitation' and 'Grade of Exploitation' refer to reducing the remaining useful lifetime of a disposable due to its usage. At the end of its lifetime, a resource is considered as being exploited. For example, a drug-filled reservoir is exploited if it is substantially empty and a battery is exploited if it does not store sufficient remaining energy for securely powering the device.

The ambulatory medical device may be a pocket-sized device and may be carried by the user frequently or continuously. Such devices are, for example, insulin pumps for Continuous Subcutaneous Insulin Infusion (CSII) and continuous as well as non-continuous glucose measuring devices as may be used in the framework of diabetes therapy.

It is believed that many alerts, in order to fulfill their intended purpose, do not necessarily have to be generated at a specific point in time but may be generated within a time interval of, for e.g., several hours. In some cases, the interval may be as long as 12 hours or even longer. The time interval defines a degree of freedom for alert generation such that an alert may be generated at an especially suited point in time of the corresponding interval based on one or multiple alerting criteria.

In contrast, some state-of-the-art devices do not consider such intervals but generate an alert at exactly the point in time a pre-specified alerting condition is met, such as a battery voltage falling below a threshold battery voltage or the drug volume stored by a drug reservoir falling below a specified threshold volume.

In some examples, the alert controller is realized by electronic circuits and may especially be integral with the device controller. The device controller may comprise components well known in the art for such units, for e.g., microcontrollers, memory components, clock circuits, power management circuits, etc.

In some examples, the ambulatory medical device is adapted to transmit alert triggers to an external device such as a cell phone or a remote controller of the ambulatory medical device. In this way, an alert may be generated on the external device. The ambulatory medical device may also comprise interface units such as a wireless RF interface unit and/or an Infra Red IR interface unit.

In some examples, the ambulatory medical device is made of at least two physically separate units, such as an administration unit and a separate controller and operation unit. These units may be adapted to exchange information and the alert controller as well as the at least one indicator may be comprised by either or multiple of the units.

In some examples, the indicator is designed to provide at least one of an optical, a tactile or an acoustic indication. Optical indication may be provided by a display but may also be provided by other optical indicators such as LED's. Audible indication and/or tactile indication may be provided, for example by a buzzer and/or a pager vibrator, respectively. In some examples, the indicator comprises an optical indicator and at least one of an audio indicator or a tactile indicator. For this type of example, the alert may comprise an audible alert and/or a tactile alert in order to draw the user's attention to the occurrence of the alert. Further information with respect to the alerting condition, such as an identification of the alerting cause, may be provided by an optical indicator, for e.g., a display.

The point in time where the alerting criterion is met defines the point in time where an alert trigger is generated within the running first alerting interval. An alerting interval is referred to as 'running' in the time interval which is limited by the earliest and the latest point in time for an alert generation. As will be discussed below in more detail, the alerting criterion may, for example, be met if a second alerting interval for a second alerting cause is ending while the first alerting interval is running. This can allow for the overall number of different points in time at which alerts are generated can be reduced, thus increasing the user convenience. In another example, the alerting criterion is met at a point in time within a running alerting interval that is especially suited for an alert generation from the user's point of view. In general, the alerting interval and alerting criterion combination takes into account that alerts have to be generated within a certain timeframe which is given by the alerting interval, but allows some flexibility with respect to the exact point in time.

The first alerting cause may be the occurrence of any situation which shall be communicated to the device user but is not time-critical and does not require an immediate action. The earliest and the latest point in time for an alert generation define the time interval in which an alert due to the first alerting cause should be generated. Within this interval, the exact point in time is defined according to the alerting criterion. The term 'within' may also include the end points of the time interval, i.e., the earliest and the latest point in time for the alert generation. The determination of alerting intervals will be apparent to those of ordinary skill in the art in view of the teachings herein.

In some examples, the first alerting cause is approaching exploitation of a disposable and the first alerting interval reflects an earliest and a latest grade of exploitation for replacing the first disposable. An alert which is triggered by the approaching exploitation of a disposable may be referred to as 'Exploitation Alert' and a corresponding alerting interval as 'Exploitation alerting interval' for clarity reasons.

The earliest point in time for generating an alert may be given when the grade of exploitation is still low but sufficiently high to justify replacement without substantial waste of the remaining life of the disposable. The latest point in time for generating the alert may be given when the disposable is substantially exploited, thus requiring immediate or soon replacement. The latest point in time, however, may also be chosen somewhat before this condition is met since it may not be possible and/or convenient for the user to replace the disposable immediately when the alert is generated.

In some examples, the disposable may be either an energy storage, such as, a battery, a drug reservoir, an infusion line, an infusion cannula, a valve, a sealing, or a glucose measurement probe Sealings, such as O-ring sealings, are used in some ambulatory medical devices to prevent fluids, especially water, as well as dust from entering the device. Valves are used, among others, to improve the safety of insulin pumps and have to be regularly replaced in order to prevent hazards such as contamination or clogging of fluid channels.

For some disposables, the lifetime is substantially constant. This is typical, for example, for infusion lines and cannulas as used in CSII, or for electrochemical glucose measurement probes as used for continuous glucose monitoring. For those disposables, the grade of exploitation may be monitored by timers which are reset when the disposable is replaced. The earliest and the latest point in time for the alert generation may be determined by comparing the past usage time or the maximum remaining usage time till exploitation with an early alerting threshold time and a late alerting threshold time. In combination, the two threshold times define the corresponding alerting interval.

Because the lifetime of many disposables is to some degree dependent on factors such as the average ambient temperature and personal factors such as skin irritation resulting from plaster adhesives, the thresholds are advantageously parameters which may be set and/or modified by the user and/or a healthcare professional.

For other disposables, such as batteries or drug cartridges, the lifetime is largely dependent on the user's individual therapy, lifestyle and habits. The insulin consumption of a diabetic person, for example, varies in a large range between persons and also from day to day, the insulin consumption affecting both the lifetime of the insulin reservoir and the energy source, especially a battery. The lifetime of typical energy sources is further dependent on factors such as the usage of a provided display backlight and the amount of wireless RF communication with external devices.

For monitoring the grade of disposable exploitation, the alert controller advantageously comprises a disposable monitoring unit which is configured to measure or compute the grade of exploitation in a continuous or cyclic way. The alert controller advantageously further comprises an exploitation computation unit which is operatively coupled to the disposable monitoring unit and determines the alerting interval, for example by comparing the grade of exploitation with an early alerting threshold and a late alerting threshold, respectively. The operation of disposable monitoring units and exploitation computation units will be apparent to those of ordinary skill in the art in view of the teachings herein.

In some examples, the alert controller is configured to determine a second alerting interval, the second alerting interval defining an earliest point in time and a latest point in time for an alert generation due to a second alerting cause, and to detect an overlap interval of the first alerting interval and the second alerting interval. The alerting criterion is provided such that the alert is generated in the overlap interval and the alert is a common alert for the first alerting cause and the second alerting cause and the indicator is configured to indicate the first alerting cause and the second alerting cause.

An alert can be generated within an alerting interval to more than one alerting cause. As will be seen below, the alert may be generated to any number of alerting causes. This can allow the reduction in the overall number of alerts that are generated at different points in time.

The information with respect to the alerting causes may be provided by an alphanumeric or numeric information on a display, but may also be provided by other optical indicators, such as a set of LEDs, by activating an acoustical and/or a tactile indicator according to an interval identifying the alerting causes, or the like.

The second alerting cause may especially be approaching exploitation of a second disposable and the second alerting interval reflecting an earliest alerting grade of exploitation and a latest alerting grade of exploitation of the second disposable.

In some examples which involve the consideration of a second alerting cause, the alerting criterion is provided such that the alert triggers are generated at the end of either of the first alerting interval or the second alerting interval, respectively.

The rationale is based on the following considerations:
(a) As long as the grade of exploitation of either of the disposables is too low to justify its replacement, an alert should not be generated for the replacement of that disposable, indicated by a corresponding exploitation alerting interval having not yet started.
(b) An exploitation alert should be generated for the replacement of that disposable if it is almost fully exploited, indicated by the ending of the corresponding exploitation alerting interval. Here, an alert is generated independent of the other disposable.
(c) In the alerting interval between the earliest and the latest grade of exploitation, an exploitation alert with respect to either of the disposables does not yet need to be generated. But it may be generated without a replacement of the disposable resulting in an exhaustive waist of lifetime of the disposable. An alert may especially be generated if an exploitation alert for another disposable has to be generated anyway. In this case, the alert is a common alert.

It will be apparent to those of ordinary skill in the art in view of the teachings herein that the role of the first alerting cause and the second alerting cause are equitable and interchangeable. In addition, the approach can applied to any number of alerting causes. Therefore, the term 'alerting cause' refers to any alerting cause in the following.

Alert generation is generally not equally convenient and acceptable for the user for all points in time. In particular, the generation of an alert may be judged as inconvenient and disturbing during night time. In some examples, the alerting criterion therefore comprises a time-dependent user acceptance of the generation of alerts. In the following, the user acceptance of the generated alert (or alert generation) is referred to as 'user acceptance' where no ambiguity may arise.

In some examples which involve the consideration of user acceptance, it is considered in a binary way. Here, high user acceptance indicates that the generated alert is accepted while low user acceptance indicates that generated alert is undesired and/or not accepted at a given point in time.

In some examples considering user acceptance, the alert controller is configured to detect an overlap interval of high user acceptance and a second alerting interval. The alert controller is configured to generate an alert trigger in the overlap interval.

In examples considering both the user acceptance and the acceptance of a disposable replacement with respect to exploitation in a binary way, the alert controller may especially be configured to generate an alert trigger when an overlap interval of an alerting interval and an interval of high user acceptance ends. This is the case when the user acceptance changes from 'high' to 'low', assuming that at least one alerting interval is running at that point in time. In this way, an alert which would generally occur at a point in time where user acceptance is low can be changed to that point in time where user acceptance changes from 'high' to 'low'. This is the latest point in time where a generated alert (or alert generation) is accepted by the user and the disposable has already been exploited to a grade which justifies its replacement. However, an alert should further be generated when an alerting interval ends independent of the user acceptance.

Some examples which consider user acceptance, the device comprises a user acceptance storage which is configured to store a user acceptance profile. The user acceptance profile is indicative of the user acceptance as a function of time. Therefore, the day may, e.g., be divided into a number of equal intervals and a corresponding value for the user acceptance may be stored by the user acceptance profile storage for each of the intervals.

The times of day which are convenient and accepted by the user for the generated alert (or alert generation) may be different for working days and for weekends. Similarly, they may be different for different days, e.g., if the user is a shift worker. Therefore, the user acceptance storage may comprise a set of storages for a set of user acceptance profiles, each user acceptance profile defining the user acceptance dependent on the time of day. The administration device (or other ambulatory medical device) may be adapted for manually changing between the user acceptance profiles based on user input and/or automatically changing between the user profiles based on changing rules.

In some examples, the device controller is configured to store a history and the alert controller is configured to modify the user acceptance profile based on data stored in the history.

The history may store information with respect to a variety of events, such as the on-demand administration of drug boli, the occurrence of error states, the replacement of a drug reservoir, device reprogramming, and the like. The occurrence of an event is stored along with a time stamp. This information may advantageously be used to modify the user acceptance profile. Because many of the events involve a user operation, such as the on-demand administration of drug boli, the user acceptance may be assumed to be low at times of rare user operations.

A history may be statistically evaluated by a history evaluation unit to determine time patterns, such as times of day, which indicate frequent and/or regular user operations. For this purpose, the 24 hours of the day may be segmented into a number of intervals, each having a duration of, e.g., 30 min, and the past average number of user operations may be determined for each interval. Intervals of high user acceptance may be determined, for example, by defining at least one threshold user operations number and assuming high user acceptance at intervals showing an average user operations number exceeding the threshold user operations number and/or by determining intervals of maximum user operations. Adoption of the user acceptance profile may be performed continuously and/or only during a learning period of, e.g., some weeks.

In some examples, the alert controller is configured to temporarily modify the user acceptance in accordance with data provided via a user interface and/or a data interface of the ambulatory medical device.

In some examples, a user interface and/or a data interface of the device is configured to receive data defining a modification time interval, and the alert controller is configured to temporarily modify the user acceptance for that modification time interval.

Such temporary modification of the user acceptance may be performed by the user, for example, by first entering a modification duration or a modification end time and second setting the user acceptance to 'low' for the modification duration or until the entered modification end time, respectively. A temporary modification of user acceptance is advantageous in spontaneously occurring situations of low user acceptance for the generated alert (or alert generation), for example when attending a meeting, being in a concert, or the like.

In some examples involving user acceptance, the user acceptance is modified on at least one of the occurrence of a user interaction with the ambulatory medical device, the occurrence of an error state, and the resolving of an error state.

Any kind of user interaction with the ambulatory medical device indicates that the user is in interaction with the device and may accordingly accept alerts even if the general user acceptance is currently low. This is the case, for example, if the user commands the administration of an insulin bolus during nighttime on an evening which differs from the user's usual habits. In some examples, the user acceptance may be modified only for a defined subset of user operations. If the user, for example, administers an insulin bolus during nighttime, he may not have gone to bed and may accordingly accept alerts. The backlight, on the contrary, may be switched on by the user just for reading the device clock while the user is in bed. Here, the user may not be willing to accept the generation of an alert which could also be generated the following morning.

In some examples, the alert controller comprises a prediction unit which is configured to predict at least one of an alerting interval or an alerting point in time. The term 'Predicting an interval' means predicting the point in time the interval starts and/or the point in time the interval ends. For predicting alerting intervals with respect to the exploitation of disposables, the prediction unit may be adapted to predict the grade of exploitation of the disposables as a function of time.

By predicting alerting intervals, the alerting times may be further optimized. Predicting alerting intervals may be particularly useful when considering user acceptance, wherein the user acceptance may be predicted, too. If the prediction indicates the generation of an alert at a future point in time of predicted low user acceptance, e.g., during the night, the generated alert (or alert generation) may be changed to an earlier point in time or delayed to a later point in time where the user acceptance is high. It should be noted that predicting user acceptance as stored by a present user acceptance profile is exact and straight-forward, as long as the user acceptance is not modified.

The exploitation of many disposables may not be independent from the time of day. Therefore, a prediction unit may be adapted for prediction dependent on the time of day. For example, a basal insulin administration profile is variable over the time of day and insulin boli are administered by an insulin pump in CSII therapy mainly at meal times. The administration affects both the remaining drug volume which is stored by a drug reservoir and the energy stored by an energy storage. Similarly, other operations requiring considerable amounts of energy, such as activating a display backlight or performing wireless communication with remote devices is likely to be, at least in part, dependent on the time of day. The time of day may be considered based on a predefined exploitation model dependent on the time of day, the exploitation model being factory set and/or provided by the user and/or a healthcare professional.

In some examples involving a predication unit, an additional history evaluation unit is present. The history evaluation unit is configured to evaluate data stored in a history of the device controller with respect to past disposable exploitation. Here, the prediction unit is configured for adaptive prediction in accordance with the history evaluation.

Prediction may be performed, for e.g., based on the average exploitation of a disposable independent of the time of day, such as past drug administration and/or past energy consumption. In addition or alternatively to the average exploitation, other criteria such as past exploitation maxima or a given quartile, e.g. the 75% quartile of past exploitation of a disposable within a given interval may be considered.

Alternatively to adaptive prediction, the history evaluation unit may be configured to evaluate the data stored in the history for a learning period of, e.g., some weeks in order to adjust an exploitation model.

In some examples, the device controller is adapted to control the at least one indicator of the device to generate reminder alerts which may be used to remind the user, e.g., to take in food some time after administering an insulin bolus or to measure his blood glucose value some time after food intake. For such examples, an alerting interval may be a reminder alerting interval which is determined by a corresponding reminder alerting cause. Reminder alerting intervals may be associated with corresponding reminder alerting signals which may be generated by a clock circuit of the ambulatory medical device and may be defined in an analog way as described above for resource alerting signals. Reminder alerts may, mutatis mutandis, be considered in an analog way as alerts which are associated with disposable exploitation.

Further examples of ambulatory medical devices may be derived from the examples described below with reference to the figures.

FIG. 1 schematically shows the internal structure of a miniaturized administration device (an exemplary ambulatory medical device), especially of an insulin pump as it may be used for diabetes therapy by CSII.

The administration device comprises a drug reservoir 20, an infusion line 25, and an infusion cannula 27 which is placed in the subcutaneous tissue. The drug reservoir 20 may, for example, be a cylindrical cartridge storing a maximum of 3.15 ml of insulin, with each ml of insulin corresponding to 100 International Units (IU). The drug (e.g., insulin) from drug reservoir 20 is expelled via a pump unit 60.

The exemplary administration device (or other ambulatory medical device) may comprise a user interface 50 with a keyboard 40, a display 30, an acoustic indicator 33, such as a buzzer and a tactile indicator 35, such as a pager vibrator.

The operation of the administration device is controlled by the device controller 80. The device controller 80 is realized as an electronics circuit with one or multiple micro controllers, static and dynamic memory, a clock circuit, a power circuit for controlling the pump unit 60, safety circuits, and the like.

The device controller 80 is connected to a rechargeable or non-rechargeable battery 85 as energy supply.

The administration device (or other ambulatory medical device) further comprises two bidirectional data interfaces, namely an Infra Red IR data interface 90 and a Radio Frequency RF data interface 95, for configuration, remote control and data exchange purposes.

The exemplary administration device (or other ambulatory medical device) further comprises an alert controller 100, 100' which is operatively coupled to the device controller 80. The functional components of the alert controller 100, 100' may be realized integral with the device controller 80. The alert controller 100, 100' comprises an alert trigger unit 130, 130' (shown in FIG. 2 and FIG. 4) as well as supplementary components used in combination with the alert trigger unit 130, 130'.

It should be noted that the examples only consider two disposables, namely a drug reservoir and a battery. These disposables are of particular importance in the framework of diabetes therapy. However, the examples may be extended and modified to consider any number of disposables dependent on the specific ambulatory medical device. Insulin pumps for example, may comprise lifetime timers for disposables such as cannulas, infusion lines, valves and sealings having a fixed lifetime as described above in the general description of the invention. The examples may further be extended to consider reminder alerts as described above.

Figure 2:
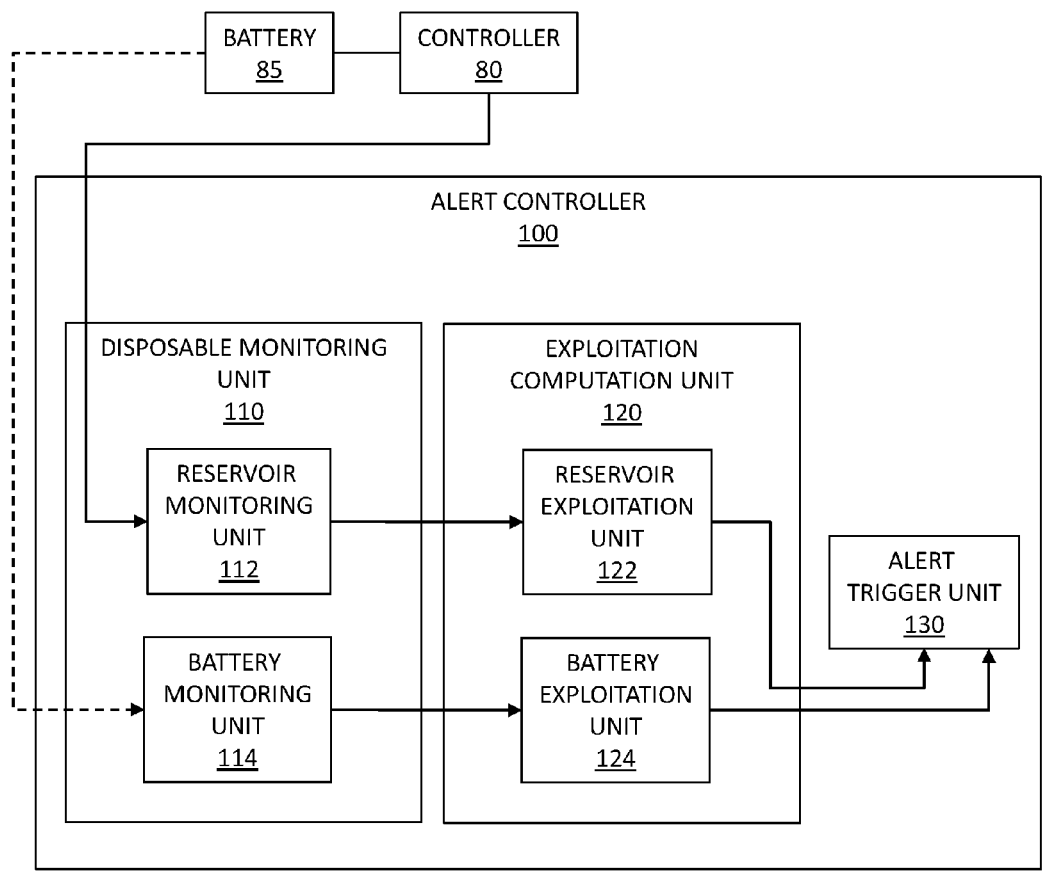
FIG. 2 depicts an exemplary arrangement of an alert trigger unit in connection with supplementary components for the ambulatory medical device of FIG. 1.

FIG. 2 shows a more detailed structural view of an exemplary alert controller 100 along with the device controller 80 and the battery 85 as shown in FIG. 1. The alert controller 100 comprises a disposable monitoring unit 110, an exploitation computation unit 120, and an alert trigger unit 130. The disposable monitoring unit 110 comprises a reservoir monitoring unit 112 and a battery monitoring unit 114. The exploitation computation unit 120 comprises a reservoir exploitation unit 122 and a battery exploitation unit 124.

The reservoir monitoring unit 112 is adapted to compute the volume of insulin stored by the drug reservoir 20 as a function of time. For computing the volume, the reservoir monitoring unit 112 is operatively coupled to the device controller 80 to receive information about the initial insulin volume which is stored in a fresh reservoir and to further receive information with respect to the insulin volume administered from the reservoir. In a slightly modified example, the reservoir supervising 112 unit is operatively coupled to or comprises a reservoir volume measurement unit, the reservoir volume measurement unit being adapted to measure the volume as a function of time.

The reservoir monitoring unit 112 is operatively coupled to a reservoir exploitation unit 122, the reservoir exploitation unit 122 and being adapted to compute a binary reservoir alerting signal. The reservoir alerting signal is computed by comparing the drug volume V in the reservoir with an early reservoir threshold volume and a late reservoir threshold volume. For a standard insulin cartridge having an initial volume of $V_0=315$ IU, an early reservoir threshold volume may be, e.g., 40 IU and a late reservoir threshold volume may be, e.g., 15 IU. The early reservoir threshold volume and the late reservoir threshold volume may be set or modified by the user and/or a healthcare professional via the user interface 50 and/or the data interfaces 90, 95. In combination, the early reservoir threshold volume and the late reservoir threshold volume define a reservoir alerting interval.

The early reservoir threshold volume may especially be set depending on the user's basal insulin demand and may be, for example, 1.5-fold or 2-fold of the basal insulin demand. This is based on the fact that, for many diabetics, the basal insulin demand is approximately half of the total daily insulin demand. Setting the early reservoir threshold volume, for example, to the two-fold of the known basal demand, results in the corresponding alerting interval beginning about one day before the cartridge is actually exploited.

The battery monitoring unit 114 is adapted to compute or determine a measure of the amount of energy which is stored by the battery 85 as a function of time. This may be done by various methods which are known in the art, such as integrating the battery current over time and/or measuring the battery voltage as a function of time. Further factors such as the ambient temperature and/or the number of charging cycles in the case of the battery 85 being rechargeable. Advanced methods for determining the remaining capacity of a battery which are particularly suited are known in the art as 'fuel gauging' and may be used as well. In examples where the battery is a standard battery, the battery monitoring unit 114 may be integral with the device controller 80. In examples where the battery 85 is a rechargeable battery, the battery monitoring unit 114 may, totally or in part, be comprised by the battery 85, such that the battery and the battery monitoring unit, in combination, form an 'intelligent' power pack.

The battery monitoring unit 114 is operatively coupled to a battery exploitation unit 124, the battery exploitation unit 124 being comprised by the exploitation computation unit 120 and being adapted to compute a binary battery alerting signal based on a measure of the remaining energy which is stored by the battery 85. The computation may be done in an analog way to the reservoir alerting signal.

The battery alerting thresholds may be, e.g., set such that the early battery alerting threshold is passed at about 40% of the initial energy and the late battery alerting threshold is passed at about 20% of the initial energy which is stored by a fresh and/or fully charged battery.

When computing the battery alerting signal, the energy which is stored by the battery may be assumed to have fallen below an alerting threshold if it has fallen below the corresponding threshold for the first time. Due to computational errors, battery recovery, temperature changes, and the like, the measured or computed energy stored by the battery may rise above the corresponding threshold which should not be considered.

The battery alerting signal and the reservoir alerting signal reflect the beginning and the end of the battery alerting interval and the reservoir alerting interval, respectively. In the following, they are assumed to be defined such that the value of the corresponding signal is Boolean '1' in the corresponding exploitation alerting interval and is Boolean '0' otherwise. Other representations, however, may be equally used.

Using this signal definition, the alert trigger unit 130 is adapted to generate an alert trigger upon the falling edge of either of the battery alerting signal or the reservoir alerting signal. A binary alert trigger signal is determined by the alert trigger unit 130, such that the value of the alert trigger signal is generally constant, e.g., '0' and defines the alert trigger as a pulse of the opposite Boolean value, e.g., '1'. The alert trigger signal is fed into the device controller 80 of the administration device (or other ambulatory medical device) along with further information, in particular information being indicative for the alerting cause or alerting causes, i.e., the disposable or disposables for which exploitation is approaching.

Upon generation of an alert trigger, the device controller 80 controls the indicators 30, 33, 35 to generate an alert which is indicative for the approaching exploitation. The alert comprises an acoustic indication via the acoustic indicator 33 and/or the tactile indicator 35. The alert further comprises a visual indication via the display 30.

The alert trigger unit 130 is adapted to perform its operation above repeatedly and substantially continuously with a computation interval of, e.g., 1 sec or a fraction of a second. For this purpose, the alert trigger unit 130 as well as the supplementary components of the alert controller 100 is adapted to receive computation triggering pulses from the device controller 80. The alert controller 100 is further adapted to operate on the occurrence of triggering events such as a user interaction with the administration device (or other ambulatory medical device) and/or the occurrence of an error state of the administration device (or other ambulatory medical device).

Figure 3:
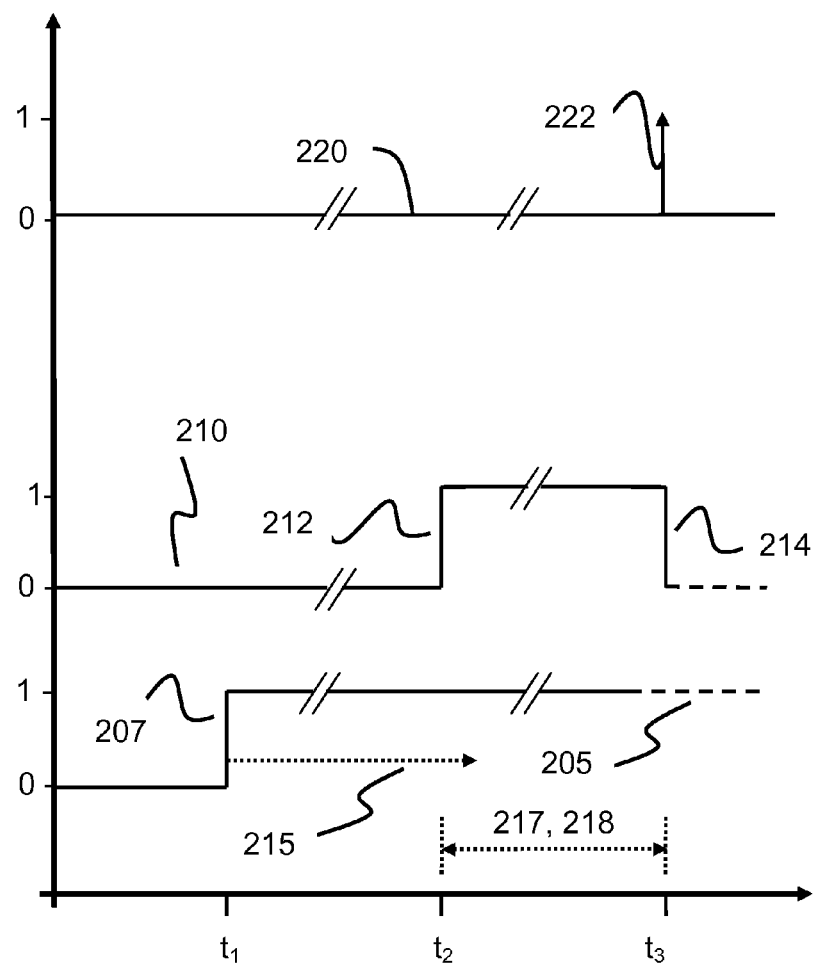
FIG. 3 depicts an exemplary course of different signals for the exemplary arrangement of FIG. 2.

FIG. 3 shows an exemplary course of the battery alerting signal 205, an exemplary course of the reservoir alerting signal, 210, and an exemplary course of the alert trigger signal, 220.

At a first point in time, $t_1$, the energy which is stored by the battery 85 falls below the early battery alerting threshold energy. Consequently, the battery alerting signal changes from '0' to '1', as indicated by the rising edge 207. At a second point in time, $t_2$, the drug volume which is stored by the drug reservoir 20 falls below the early reservoir threshold volume. Consequently, the reservoir alerting signal changes from '0' to '1', as indicated by the rising edge 212. At a third point in time, $t_3$, the drug volume falls below the late reservoir threshold volume. Consequently, the reservoir alerting signal changes from '1' to '0', as indicated by the falling edge 214. The rising edge 212 and the falling edge 214 of the reservoir alerting signal 210 define a reservoir alerting interval 217, which, in this specific example, also is an overlap interval 218. The falling edge 214 of the reservoir alerting signal 210 triggers the generation of a positive pulse 222 of the alert trigger signal 220. The pulse 222 serves as alert trigger. Accordingly, the third point in time $t_3$ is an alerting point in time and the device controller 80 triggers the generation of an alert by the indicators 30, 33, 35. The alert indicates that the drug reservoir 20 should be replaced soon and the battery 85 may be replaced along with the drug reservoir 20 with an acceptable grade of exploitation.

Figure 4:
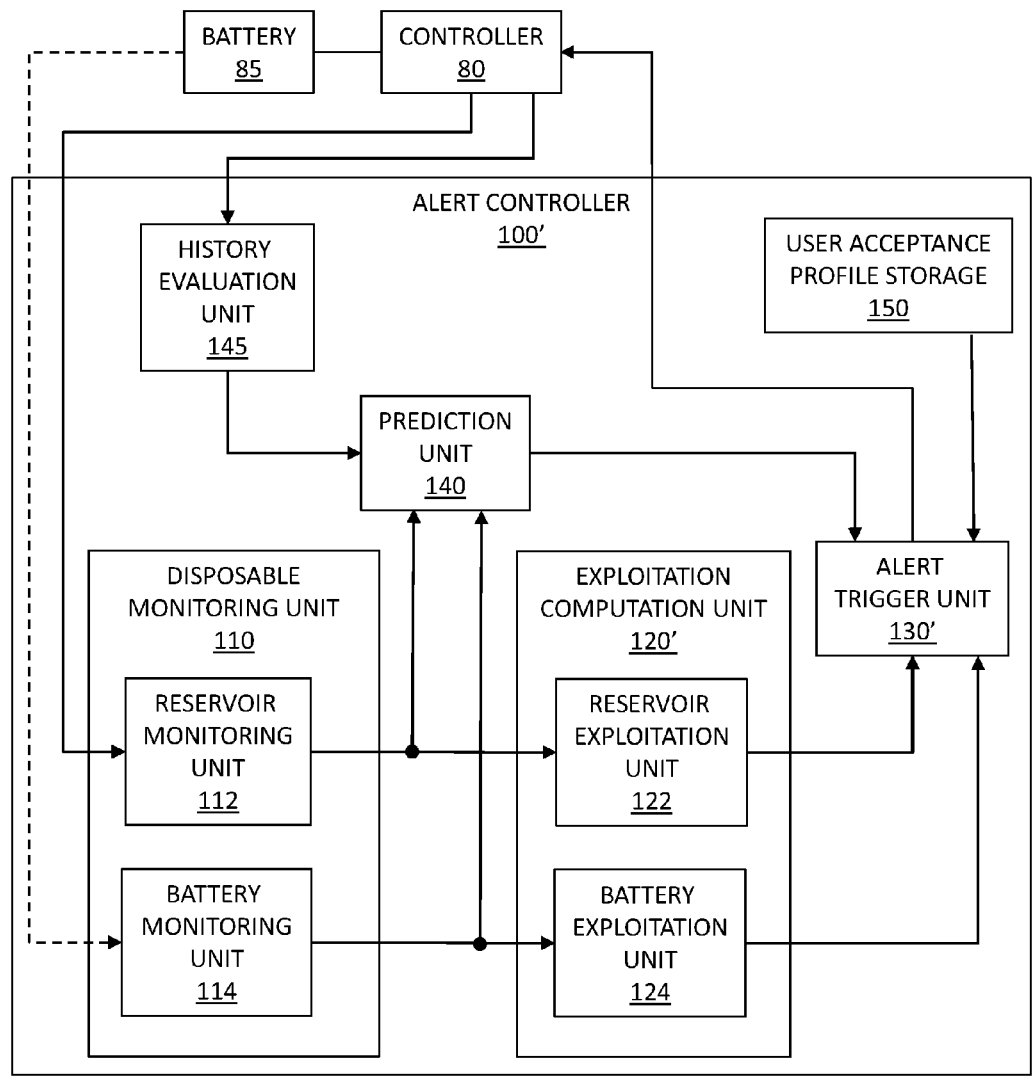
FIG. 4 depicts an exemplary arrangement of an alert trigger unit in connection with supplementary components for the ambulatory medical device of FIG. 1.

FIG. 4 shows a structural view of a further exemplary alert controller 100' along with the device controller 80 and the battery 85 as shown in FIG. 1. Since some of the elements of the alert controller 100' are substantially identical with the alert controller 100 as described above, the following description of the alert controller 100' and its operation is largely focused on such components and operational steps which are not present in the previously described example and/or operate in a substantially different way. This is especially the case for the alert trigger unit 130'.

The alert controller 100' comprises a history evaluation unit 145 which is adapted to statistically evaluate data that are stored in a history stored by the memory of the device controller 80. Among others, the history especially stores information with respect to past drug administration and with respect to past energy consumption and/or data from which this information can be derived.

The prediction unit 140 is adapted to predict the course of the exploitation alerting signals, namely of the reservoir alerting signal and the battery alerting signal. The prediction is carried out based on the data provided by the disposable monitoring unit 110 and on prediction data supplied by the history evaluation unit 145.

Prediction is performed by the prediction unit 140 for a prediction time period $T_{predict}$ of, e.g., 24 h. The prediction time period $T_{predict}$ is divided into $N_{predict}$ equal prediction intervals of length $\Delta T$, with $\Delta T$ being, e.g, 15 min. For each of the $N_{predict}$ prediction intervals, the history evaluation unit computes the average past drug consumption $V_{avr\_x}$ in the corresponding x-th interval of the last $N_{history}$ days, with $N_{history}$ being the number of past days used for the statistical evaluation. Based on the average past drug consumption data $V_{avr\_x}$ and the drug volume V currently stored by the drug reservoir 20, the prediction unit 140 computes the predicted volume $V_{pred\_x}$ for the x-th prediction interval as $$V_{pred\_x}V(t)-V_{avr\_x}.$$

The predicted course of the drug volume is a step function which the predicted volume being constant within each prediction interval. In slightly modified, a linear or non-linear extrapolation may be performed.

The energy which is stored by the battery 85 may be predicted by the prediction unit in substantially the same way as the drug volume. For this purpose, the history stores the energy which is currently stored by the battery 85 and/or the consumed energy as determined by the battery monitoring unit 114 for at least the $N_{history}$ past days. In slightly modified examples, the consumed energy is, totally or in part, determined based on a mathematical energy consumption model. Alternatively or additionally to the energy a, an indirect measure, such as the battery voltage, may be predicted.

The predicted courses of the drug volume and the energy define the predicted course of the corresponding alerting signals.

The exemplary alert controller 100' further comprises a user acceptance profile storage 150 which is operatively coupled to the alert trigger unit 130'. For this purpose, the day is divided into a set of $N_{ACC}$ user acceptance intervals, with the user acceptance interval length $\Delta T_{ACC}$ being given by 24 h/$N_{ACC}$. The user acceptance profile storage 150 stores a set of $N_{ACC}$ binary values $ACC_x$, with 'x' being a placeholder for a time interval and each value $ACC_x$ indicating the user acceptance in corresponding user acceptance interval, wherein a '0' indicates low user acceptance and a '1' indicates high user acceptance. The user acceptance interval $\Delta T_{ACC}$ is, e.g., 15 min. In slightly modified examples, the user acceptance interval length $\Delta T_{ACC}$ may be longer or shorter or the user acceptance profile storage 150 only stores the times of day where the user acceptance changes. The user acceptance profile storage 150 converts the user acceptance profile into a continuous user acceptance signal. The user acceptance profile storage 150 stores different sets of user acceptance values, with each set of user acceptance values reflecting different situations, such as working day, weekend, holiday, day shift, night shift, and the like.

Intervals where the user acceptance signal is Boolean '1' define user acceptance intervals.

In slightly extended examples, the user acceptance signal may be modified spontaneously and on demand by the user and/or based on user operations as described above.

In the following, operation of the alert trigger unit 130' and supplementary components of the alert controller 100' is described with reference to FIG. 4 through FIG. 6.

Figure 5:
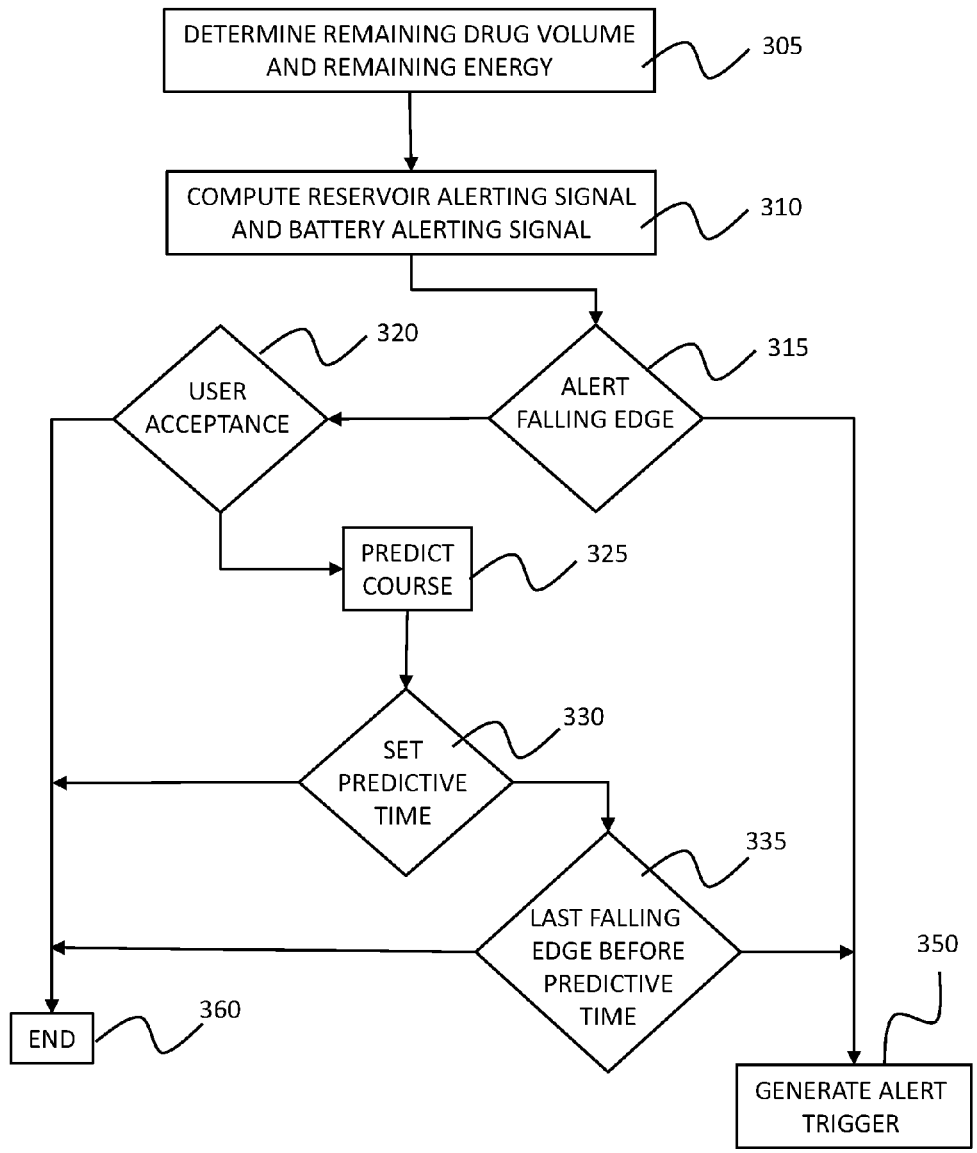
FIG. 5 depicts the major steps performed by an alert trigger unit and supplementary components for the exemplary arrangement of FIG. 4.

In step 305 of FIG. 5, the disposable monitoring unit 110 determines the remaining drug volume and the remaining energy as described above. In step 310, the exploitation computation unit 120' computes the reservoir alerting signal and the battery alerting signal on the basis of the drug volume and the energy. In step 315, a falling edge of either of the reservoir alerting system or the exploitation alerting signal is detected. In case of a falling edge, an alert trigger is generated in step 350 as a positive pulse of an alert trigger signal. Subsequently, an alert is generated as described above. It should be noted that in the case of a falling edge of either of the alerting signals an alert trigger is generated independent of the user acceptance signal.

In step 320, a falling edge of the user acceptance signal is detected, indicating the user acceptance changing from 'high' to 'low'. If no falling edge is detected in step 320, the computation ends with step 360. In case a falling edge of the user acceptance signal, the course of the exploitation alerting signals, as well as the further course of the user acceptance signal is predicted by the prediction unit 140 in step 325.

In step 330, the predicted time of occurrence of a falling edge of either of the exploitation alerting signals is set into relation to the user acceptance signal. If the predicted user acceptance is high at the predicted time, no alert trigger is generated, and the computation ends with step 360. This is indicative for a future overlap interval of a user acceptance interval and a exploitation alerting interval.

If the predicted user acceptance is 'low' at the predicted time, step 335 considers, based on the prediction of the user acceptance signal, whether the current falling edge of the user acceptance signal is the last falling edge before the predicted time. If this is the case, an overlap interval of a user acceptance interval and a exploitation alerting interval is currently ending and there will be no further overlap interval before the corresponding disposable has to be replaced at the latest. Accordingly, an alert trigger is generated in step 350. If it is not the case, there will be a future overlap interval of an alerting acceptance interval and a exploitation alerting interval before the corresponding disposable has to be replaced at the latest. Consequently, no alert trigger is generated and computation ends with step 360.

In the diagram of FIG. 5 it is assumed that all operational steps are performed with the same computation interval. In slightly modified examples, however, different operational steps or sets of steps are performed with different computation intervals. In particular, the steps 305, 310, 315 may be performed with a shorter computation interval as compared to the other steps. The steps 305, 310, 315 may be computed with a computation interval, of, e.g., 1 sec. or even shorter, while the remaining steps may be performed with a longer computation interval of, e.g., 3 min. The prediction step 325 requires the highest computational effort and may therefore be performed with an even larger computation interval of, e.g., 15 min. The alert controller 100' is further adapted to perform the steps as defined above on the occurrence of triggering events such as a user interaction with the administration device (or other ambulatory medical device) and/or the occurrence of an error state of the administration device (or other ambulatory medical device).

In one example, an alert is generated based on the same considerations as for the previously described example. However, it additionally considers that an alert should not be generated at a point in time where user acceptance is low.

Figure 6A:
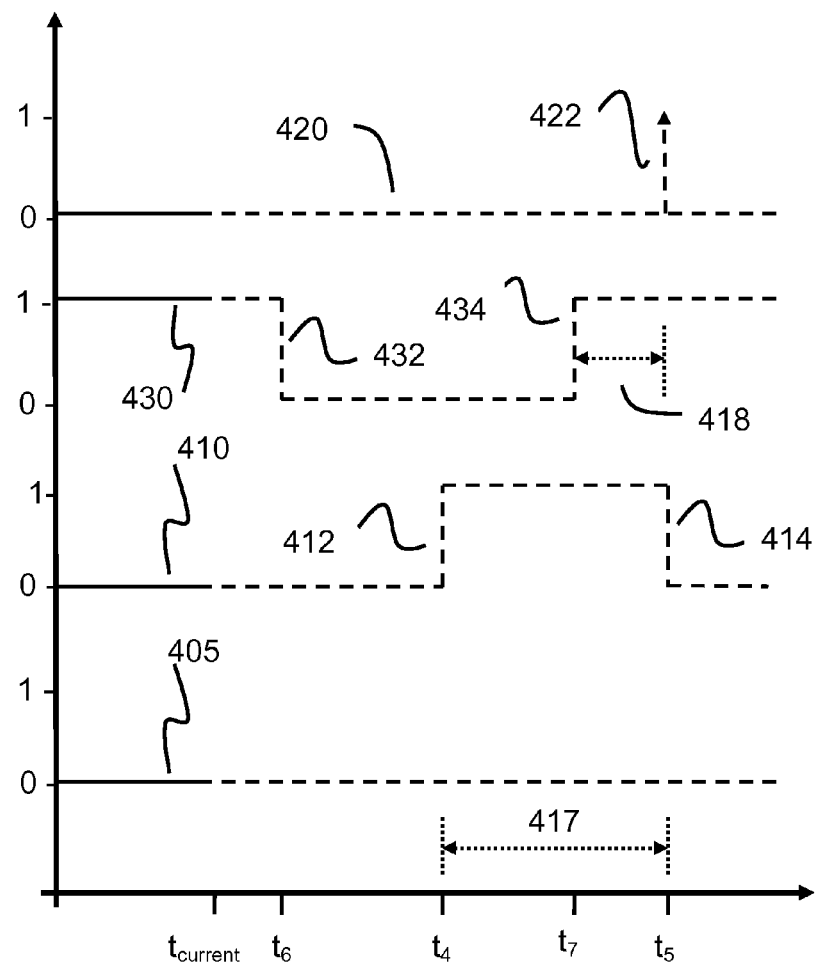
FIG. 6A and FIG. 6B depict an exemplary course of different signals for the exemplary arrangements of FIG. 4 and FIG. 5.

FIG. 6A shows an exemplary course of the battery alerting signal 405, the course of the reservoir alerting signal 410, the course of the alert trigger signal 420, and the course of the user acceptance signal 430. The course of the signals is shown for the current point in time $t_{current}$, such that all signal courses before the current point in time $t_{current}$ are past and actual signal courses, as indicated by solid lines, while all signal courses after the current point in time $t_{current}$ are future and therefore predicted courses, as indicated by dashed lines. The predicted course of the user acceptance signal 430 is identical with the course defined by the user acceptance profile as long as it is not spontaneously modified. The reservoir alerting signal is predicted to change from '0' to '1' at a predicted point in time $t_4$, as indicated by the rising edge 412 of the reservoir alerting signal 410, and back to '0' at a predicted point in time $t_5$, as indicated by the falling edge 414 of the reservoir alerting signal 410. The rising edge 412 and the falling edge 414 of the reservoir alerting signal 410, in combination, define reservoir alerting interval 417. The user acceptance is predicted to change from 'high' 'low' at a future point in time $t_6$, as indicated by the falling edge 432, and back to 'high' at a future point in time $t_7$, as indicated by the rising edge 434 of the user acceptance signal 430. The interval of low user acceptance may, e.g., correspond to night time. At the predicted point in time $t_5$, the predicted user acceptance is high. Accordingly, the future point in time $t_5$ is a predicted alerting point in time, as indicated by the positive pulse 422 of the alert trigger signal 420. The rising edge 434 of the user acceptance signal 430 and the falling edge 414 of the reservoir alerting signal 410, in combination, define a predicted overlap interval 418 at the end of which an alert is generated.

Figure 6B:
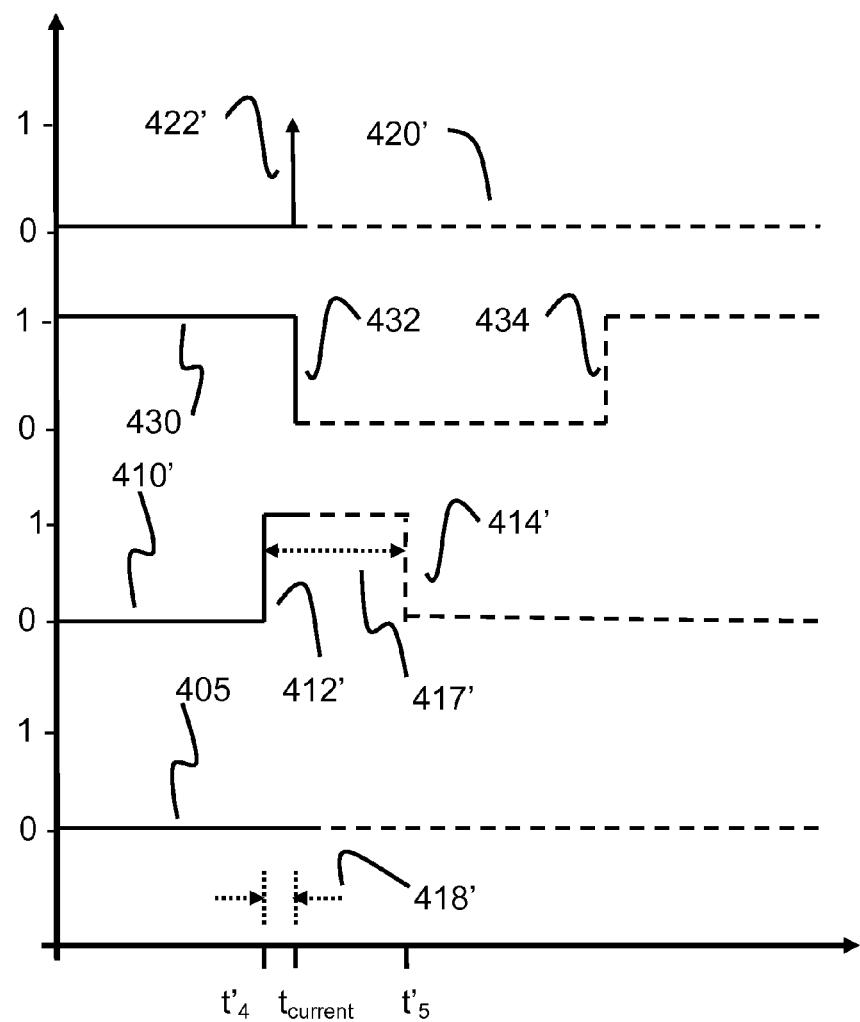

FIG. 6B shows exemplary signal courses as shown in FIG. 6A at a later current point in time, $t'_{current}$. The same reference signs are used in FIG. 6B as in FIG. 6A for elements which are not changed. Points in time and signal courses which are different as compared to FIG. 6A are indicated by an additional apostrophe. In contrast to the previous prediction, a larger amount of insulin has been administered, e.g., due to an extensive dinner. Accordingly, the reservoir alerting signal changes from '0' to '1' and from '1' back to '0' at earlier points in time $t'_4$ and $t'_5$, respectively, as indicated by the edges 412', 414' of the reservoir alerting signal 410'. Consequently, the reservoir alerting interval 417' is shorter than the reservoir alerting interval 417 which is shown in FIG. 6A. The reservoir alerting signal is predicted to change from '1' to '0' at a point in time where the user acceptance is predicted to be 'low', as indicated by the user acceptance signal 430. No later falling edge is predicted to occur for the user acceptance signal before the predicted point in time $t'_5$. Accordingly, an alert trigger is generated at the current point in time as indicated by the positive pulse 422' of the alert trigger signal 420'. In this case, the rising edge 412' of the reservoir alerting signal 410' and the falling edge 432 of the user acceptance signal 430, in combination, define an overlap interval 418' at which end the exploitation alert is generated.

It can be seen that generation of the alert (or alert generation) is avoided at a point in time where the user acceptance is predicted to be 'low', and is changed to the current point in time t_current'.

For all examples as described above, the alert controller 100, 100' is comprised by the corresponding ambulatory medical device. In slightly modified examples, the alert controller is, in total or in part, comprised by an external device, such as a remote controller, a cell phone, or the like, wherein the portable medical device and the external device are adapted to communicate with each other.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. An ambulatory medical device, comprising:
   a) a device controller, the device controller configured to control operation of the ambulatory medical device;
   b) an alert controller, the alert controller configured to:
      determine a first alerting interval, the first alerting interval defining an earliest point in time and a latest point in time for an alert generation due to a first alerting cause,
      determine in the first alerting interval an alerting point in time based on an alerting criterion, generate an alert trigger at the alerting point in time; and
   c) an indicator, the indicator configured to generate an alert upon generation of the alert trigger, wherein the alert controller is further configured to:
      determine a second alerting interval, the second alerting interval defining an earliest point in time and a latest point in time for an alert generation due to a second alerting cause, and
      detect an overlap interval of the first alerting interval and the second alerting interval,
      wherein the alerting criterion is provided such that the alert is generated in the overlap interval and the alert is a common alert for the first alerting cause and the second alerting cause and the indicator is configured to indicate the first alerting cause and the second alerting cause.

2. The ambulatory medical device of claim 1, wherein the alerting criterion is defined such that the alert trigger is generated at the end of either the first alerting interval or the second alerting interval.

3. The ambulatory medical device of claim 1, wherein the first alerting cause is approaching exploitation of a first disposable, and the first alerting interval reflecting an earliest and a latest grade of exploitation for replacing the first disposable.

4. The ambulatory medical device of claim 1, wherein the first disposable is an energy storage, a drug reservoir, an infusion line, an infusion cannula, a valve, a sealing, or a glucose measurement probe.

5. The ambulatory medical device of claim 1, wherein the second alerting cause is approaching exploitation of a second disposable and the second alerting interval reflecting an earliest and a latest grade of exploitation for replacing the second disposable.

6. The ambulatory medical device of claim 1, wherein the alerting criterion comprises a time-dependent user acceptance of the generated alert.

7. The ambulatory medical device of claim 1, further comprising a user acceptance storage, the user acceptance storage configured to store a user acceptance profile, the user acceptance profile is indicative of user acceptance of the generated alert as a function of time.

8. The ambulatory medical device of claim 7, wherein the device controller is configured to store a history and the alert controller is configured to modify the user acceptance profile based on data stored in the history.

9. The ambulatory medical device of claim 6, further comprising a user interface and a data interface, wherein the alert controller is configured to temporarily modify the time-dependent user acceptance of the generated alert in accordance with data provided via the user interface and the data interface.

10. The ambulatory medical device of claim 9, wherein the user interface and the data interface are configured to receive data defining a modification time interval, and the alert controller is configured to modify the time-dependent user acceptance of the generated alert for the modification time interval.

11. The ambulatory medical device of claim 6, wherein the alert controller is configured to modify the time-dependent user acceptance of the generated alert on at least one of an occurrence of a user interaction with the ambulatory medical device, an occurrence of an error state, or an resolving of an error state.

12. The ambulatory medical device of claim 6, wherein the alert controller is configured to detect an overlap interval of high user acceptance for the generated alert and an alerting interval, wherein the alerting criterion is provided such that the alert trigger is generated in the overlap interval.

13. The ambulatory medical device of claim 12, wherein the alerting criterion is defined such that the alert trigger is generated when the overlap interval of high user acceptance for the generated alert and the alerting interval ends.

14. The ambulatory medical device of claim 1, further comprising a prediction unit, the prediction unit configured to predict at least one of an alerting interval or the alerting point in time.

15. An ambulatory medical device, comprising:
   a) a device controller, the device controller configured to control operation of the ambulatory medical device;
   b) an alert controller, the alert controller configured to:
      determine an alerting interval, the alerting interval defining an earliest point in time and a latest point in time for an alert generation due to an alerting cause,
      determine in the alerting interval an alerting point in time based on an alerting criterion,
      generate an alert trigger at the alerting point in time; and
   c) an indicator, the indicator configured to generate an alert upon generation of the alert trigger, wherein the alerting criterion comprises a time-dependent user acceptance of the generated alert, and
      wherein the alert controller is configured to detect an overlap interval of high user acceptance for the generated alert and the alerting interval, wherein the alerting criterion is provided such that the alert trigger is generated in the overlap interval.

16. The ambulatory medical device of claim 15, wherein the alerting criterion is defined such that the alert trigger is generated when the overlap interval of high user acceptance for the generated alert and the alerting interval ends.

17. The ambulatory medical device of claim 15, further comprising a prediction unit, the prediction unit configured to predict at least one of the alerting interval or the alerting point in time.

18. The ambulatory medical device of claim 15, wherein the alerting criterion is defined such that the alert trigger is generated at the end of the alerting interval.

19. The ambulatory medical device of claim 15, wherein the alerting cause is approaching exploitation of a disposable, and the alerting interval reflects an earliest and a latest grade of exploitation for replacing the disposable, and wherein the disposable is an energy storage, a drug reservoir, an infusion line, an infusion cannula, a valve, a sealing, or a glucose measurement probe.

20. The ambulatory medical device of claim 15, further comprising a user acceptance storage, the user acceptance storage configured to store a user acceptance profile, the user acceptance profile is indicative of user acceptance of the generated alert as a function of time.

21. The ambulatory medical device of claim 20, wherein the alert controller is configured to modify the user acceptance of the generated alert on at least one of an occurrence of a user interaction with the ambulatory medical device, an occurrence of an error state, a resolving of an error state, or in accordance with data provided via at least one of a user interface of the device, a data interface of the device, or a history stored by the device.

\* \* \* \* \*

UNITED STATES PATENT AND TRADEMARK OFFICE
CERTIFICATE OF CORRECTION

PATENT NO. : 9,047,398 B2
APPLICATION NO. : 13/025691
DATED : June 2, 2015
INVENTOR(S) : Heiner Kaufmann et al.

It is certified that error appears in the above-identified patent and that said Letters Patent is hereby corrected as shown below:

Title Page, please insert, item (30)

--Foreign Application Priority Data

Aug. 11, 2008   (EP) ..................................08014273.0--;

In the Specification

Col. 12, Line 20,
   "$V_{pred\_x} V(t) - V_{avr\_x}$." should read
   --$V_{pred\_x} = V(t) - V_{avr\_x}$.--;

Col. 2, Line 17,
   "sion of a ambulatory medical device." should read
   --sion of an ambulatory medical device.--;

Col. 3, Line 35,
   "be provided by other optical indicators such as LED's." should read
   --be provided by other optical indicators such as LEDs.--;

Col. 5, Line 55,
   "ment of the disposable resulting in an exhaustive waist of" should read
   --ment of the disposable resulting in an exhaustive waste of--;

Col. 5, Line 63,
   "changeable. In addition, the approach can applied to any" should read
   --changeable. In addition, the approach can be applied to any--;

Signed and Sealed this
Twelfth Day of April, 2016

Michelle K. Lee
*Director of the United States Patent and Trademark Office*

CERTIFICATE OF CORRECTION (continued)
U.S. Pat. No. 9,047,398 B2

Col. 13, Line 17,
"putation ends with step 360. In case a falling edge of the user" should read
--putation ends with step 360. In case of a falling edge of the user--;

Col. 14, Line 16,
"acceptance is predicted to change from 'high' 'low' at a future" should read
--acceptance is predicted to change from 'high' to 'low' at a future--;

Col. 14, Line 55,
"time t_current'." should read
--time $t_{current}$.--; and

In the Claims

Col. 16, Claim 11, Line 29,
"device, an occurrence of an error state, or an resolving of an" should read
--device, an occurrence of an error state, or a resolving of an--.